United States Patent [19]  [11]  4,341,772
Grantham  [45]  Jul. 27, 1982

[54] AGRICULTURAL PHOSPHORUS-CONTAINING SULFENAMIDES

[75] Inventor: Gary D. Grantham, Wilmington, Del.

[73] Assignee: E. I. Du Pont de Nemours and Company, Wilmington, Del.

[21] Appl. No.: 146,420

[22] Filed: May 5, 1980

[51] Int. Cl.³ .................... A01N 57/28; A01N 57/30; A01N 57/32; C07F 9/44
[52] U.S. Cl. .................................. 424/211; 424/203; 260/465 E; 260/949; 260/951; 260/954; 568/15; 546/21; 544/157; 549/220; 548/412
[58] Field of Search .......... 260/949, 951, 954, 465 E, 260/340.7, 340.5 R; 424/211, 203; 564/15

[56] References Cited

FOREIGN PATENT DOCUMENTS

| | | | |
|---|---|---|---|
| 826376 | 9/1975 | Belgium | 564/433 |
| 846205 | 3/1977 | Belgium | 564/433 |
| 846419 | 3/1977 | Belgium | 564/433 |
| 156 | 1/1979 | European Pat. Off. | 564/433 |
| 4642 | 10/1979 | European Pat. Off. | 564/433 |
| 1455207 | 11/1976 | United Kingdom | 564/433 |

Primary Examiner—Alan L. Rotman

[57] ABSTRACT

S-(Diarylamino)thiophosphates are useful as miticides, insecticides, fungicides and ovicides.

45 Claims, No Drawings

AGRICULTURAL PHOSPHORUS-CONTAINING SULFENAMIDES

BACKGROUND OF THE INVENTION

This invention relates to miticidal, insecticial, fungicidal and ovicidal diarylsulfenamides.

Belgian Pat. No. 826,376 discloses pesticidal diphenylamine derivatives of the formula:

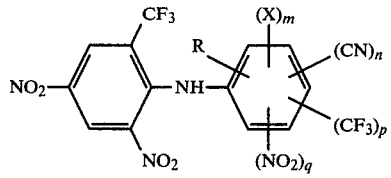

where X and R represent various substituents definitions; and British Pat. No. 1,455,207 discloses a pesticidal diphenylamine of the formula:

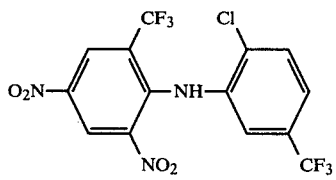

Belgian Pat. No. 846,205 discloses compounds with utility as rodenticides of the formula

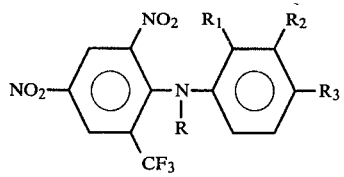

where R, $R_1$, $R_2$ and $R_3$ represent various defined substituents.

Belgian Pat. No. 846,419 discloses compounds with utility as delayed-action rodenticides.

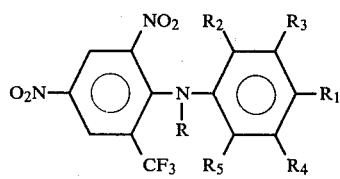

where R, $R_1$, $R_2$, $R_3$, $R_4$ and $R_5$ represent various defined substituents.

European Patent No. 156 discloses benzotrifluoride derivatives with insecticidal, acaricidal, nematicidal, insect growth retardant, fungicidal and bactericidal activity. These compounds have the formula

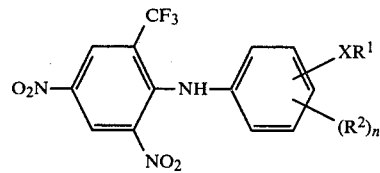

where $R^1$ and $R^2$ represent various defined substituents.

European Patent No. 4642 discloses compounds useful as insecticides, acaricides, nematocides, fungicides and herbicides of the formula

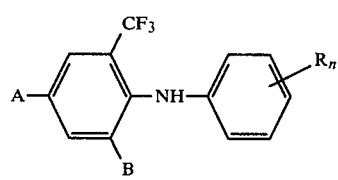

where A, B and R represent various defined substituents.

SUMMARY

According to this invention, compounds of the following formula have been discovered which are highly active miticides, insecticides, ovicides, and/or fungicides, and which cause minimal damage to desired crops.

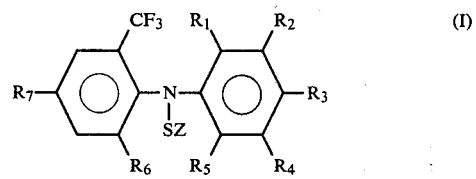

wherein $R_1$, $R_3$ and $R_4$ are independently H, F, Cl, Br, $NO_2$, $CF_3$, $OCHF_2$, $OCF_3$, $OCF_2CF_2H$ or $S(O)_kR_8$; or $R_3$ and $R_4$ may be taken together to form —$OCF_2O$— or —$OCF_2OCF_2$—;

$R_2$ is H, F, Cl, Br, $NO_2$, $CF_3$ or $S(O)_kR_8$;

$R_5$ is H, Cl, F, Br or $NO_2$;

$R_6$ is H, $NO_2$ or $CF_3$;

$R_7$ is $NO_2$ or $CF_3$; k is 0, 1 or 2;

$R_8$ is $C_1$-$C_2$ alkyl optionally substituted with 2-4 Cl and/or F;

Z=

X is O or S;

$Y_1$ or $Y_2$ are independently: $C_1$-$C_4$ alkyl optionally substituted with one or more F, Cl, Br, I, $OCH_3$, $OCH_2CH_3$, CN, $CH_3S$, $CH_3CH_2S$; $C_2$-$C_4$ alkenyl optionally substituted with one or more F, Cl, carboxy or carboalkoxy; benzyl which can be optionally substituted with F, Cl, Br, I, $NO_2$, $CH_3$, $OCH_3$ or $CF_3$; $C_1$-$C_4$ alkoxy optionally substituted with one to three atoms of F, Cl, Br, $CH_3O$, $CH_2CH_2O$ or combinations thereof; $C_1$-$C_4$ thioalkyl optionally substituted with one to three atoms of F, Cl, Br, I, carboxy or carboalkoxy, or combinations thereof; phenyl, phenoxy or thiophenoxy each optionally substituted with one to three atoms of F, Cl, Br, I, NO, $CH_3$, $CF_3$ or combinations thereof; $NR_{10}R_{11}$ where $R_{10}$ is $C_1$-$C_4$ alkyl or $OCH_3$;
$R_{11}$ is $C_1$-$C_4$ alkyl and
$R_{10}$ and $R_{11}$ can be taken together to form

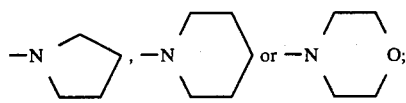

$Y_1$ and $Y_2$ can be taken together to form

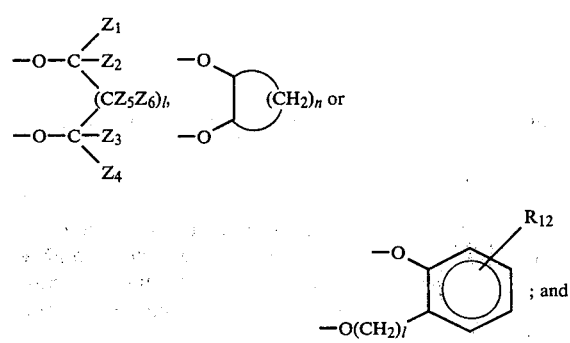

$R_{12}$ is H, $C_1$-$C_4$ alkyl, $C_1$-$C_4$ alkoxy, or halogen; where $Z_1$, $Z_2$, $Z_3$, $Z_4$, $Z_5$ or $Z_6$ are independently H, $CH_3$ or $CH_3CH_2$;

n is 3 or 4;
l is 0 or 1;
provided that
(1) at least two of $R_1$, $R_2$, $R_3$, $R_4$ and $R_5$ are hydrogen;
(2) no more than two of the substituents $R_1$, $R_2$, $R_3$ and $R_4$ are simultaneously $NO_2$ or $CF_3$;
(3) when two $NO_2$ or two $S(O)_kR_8$ groups are present, they are not ortho to one another;
(4) $R_6$ and $R_7$ are not simultaneously $CF_3$; and
(5) further provided that when $R_6$ is $NO_2$, then
    (a) $R_1$ is H, F or Cl when $R_3$ is other than H, F or Cl;
    (b) when $R_1 = R_3 = R_5$, then $R_1$, $R_3$ and $R_5$ are either H or F; and
    (c) $R_5$ is either H or F.
(6) only one of $Y_1$ and $Y_2$ is $NR_{10}R_{11}$.

Preferred Compounds

Preferred for reasons of lower cost, lower phytotoxicity and/or greater miticidal, insecticidal, ovicidal and/or fungicidal activity are those compounds of Formula I where independently:

$R_1$ is F, Cl, Br, $CF_3$, $OCHF_2$, $OCF_3$, $OCF_2CF_2H$ or $S(O)_kCF_3$;
$R_2$ is H, F, Cl or Br;
$R_3$ is H, F, Cl, Br or $S(O)_kCF_3$;
$R_4$ is F, Cl, Br, $CF_3$, $OCHF_2$, $OCF_3$, $OCF_2CF_2H$ or $S(O)_kCF_3$; and
$R_6$ is $NO_2$.

More preferred for the same reasons are compounds of Formula I were independently:

$R_1$ and $R_4$ are independently Cl, $CF_3$, $OCF_3$, $OCF_2CF_2H$ or $S(O)_kCF_3$;
$R_3$ is H or $S(O)_kCF_3$;
$R_2$ and $R_5$ are H;
$R_6$ and $R_7$ are $NO_2$ Still More Preferred for the above reasons and in increasing order of preference are those compounds at the More Preferred in which
(1) $Y_1$ equals $Y_2$
(2) Compounds of Preference 1 in which $Y_1$ is $CH_3O$, $CH_3CH_2O$, $CH_3S$, $CH_3CH_2S$,

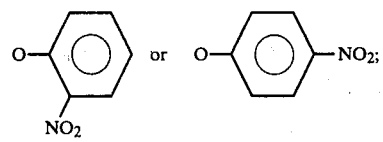

(3) Compounds of Preference 2 in which X is O.

Synthesis

The compounds of this invention can be prepared by reacting a diphenylamine of Formula II with sulfenyl chlorides, ClSZ, in the presence of an acid acceptor and an inert solvent as outlined in the following equation:

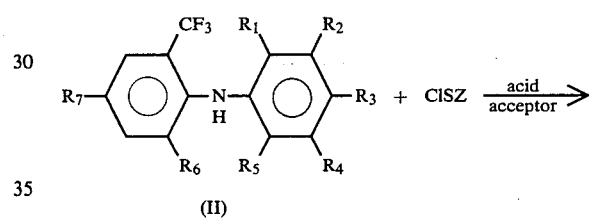

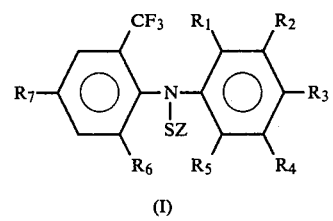

in which $R_1$, $R_2$, $R_3$, $R_4$, $R_5$, $R_6$, $R_7$ and Z are as previously defined. Organic bases such as N,N-dimethylaniline, triethylamine, trimethylamine, or pyridine or inorganic bases such as sodium or potassium hydroxide sodium or potassium carbonate, or sodium hydride may be used as the acid acceptor. Aprotic solvents such as diethyl ether, tetrahydrofuran (THF), dioxane, methylene chloride, chloroform, or toluene are exemplary of suitable solvents for the reaction. The reaction temperature can be within the range of approximately $-40°$ C. to $80°$ C., preferably approximately $-20°$ C. to $30°$ C. Pressure is not critical; for convenience, ambient pressure is preferred.

The diphenylamines of Formula II used in the reactions described above can be prepared using procedures taught in Belgian Pat. No. 826,376, West German Offenlegungsschrift No. 2,823,168, European Patent Application 156, and European Patent Application 4,642, the disclosures of which are herein incorporated by reference.

The sulfenyl chlorides, ClSZ, used in the preparation of the compounds of Formula I may be prepared by any of several methods well known in the art; such methods have been reviewed in the art; such methods have been reviewed in *Synthesis* 11, 561–580 (1970).

The following example further illustrates the preparation of compounds of Formula I. In the example, all parts are by weight and temperatures are in degrees Centigrade unless otherwise indicated.

EXAMPLE 1

S-[N-[2-Chloro-5-(trifluoromethyl)phenyl]-N-[2,4-dinitro-6-(trifluoromethyl)phenyl]amino]-o,o-diethylphosphorothioic acid Slurry sodium hydride (1.1 equivalents) in anhydrous tetrahydrofuran under a nitrogen atmosphere at room temperature. Add dropwise a solution of N-[2-chloro-5-(trifluoromethyl)phenyl]-2,4-dinitro-6-(trifluoromethyl)benzeneamine (1 equivalent) in anhydrous tetrahydrofuran with stirring. When the addition is complete, stir the solution at ambient temperature, until the reaction is complete. Add diethoxyoxyphosphoranesulfenyl chloride (1 equivalent, Tet, 31, 2809 (1975)] and continue to stir until the reaction is complete. Dilute this reaction mixture with methylene chloride, wash with water, dry (Na$_2$SO$_4$) and concentrate in-vacuo to give the crude product. Purification by a standard method to give S-[N-[2-chloro-5-(trifluoromethyl)phenyl]-2,4-dinitro-6-(trifluoomethyl)phenyl]amino]-o,o-diethylphosphorothioic acid.

TABLE I

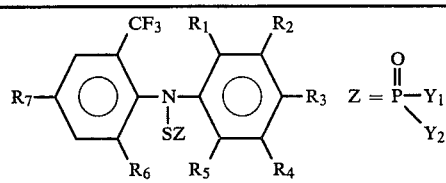

TABLE I-continued

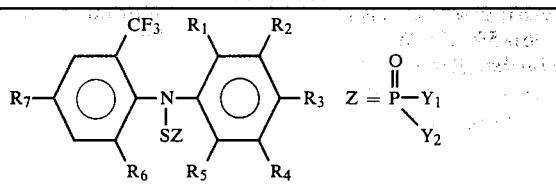

| R7 | R6 | R5 | R1 | R2 | R3 | R4 | X | Y1 | Y2 |
|---|---|---|---|---|---|---|---|---|---|
| Cl | H | H | CF3 | H | NO2 | NO2 | O | N(CH3)(OCH3) | —OCH2CH2OC2H5 |
| Cl | H | H | CF3 | H | NO2 | NO2 | O | SCH3 | —O(CH2)3CH3 |
| Cl | H | H | CF3 | H | NO2 | NO2 | O | —S—C6H4—CF3 | —(CH2)3CH3 |
| Cl | H | H | CF3 | H | NO2 | NO2 | O | OCH3 | SCH3 |
| Cl | H | H | CF3 | H | NO2 | NO2 | O | —OCH2CH2SCH3 | —OCH2CH2SCH3 |
| Cl | H | H | CF3 | H | NO2 | NO2 | O | piperidino | —C6H4—CH3 |
| Cl | H | H | CF3 | H | NO2 | NO2 | O | morpholino | —O—C6H4—F |
| Cl | H | H | CF3 | H | NO2 | NO2 | O | —O—C6H3(Cl)(Cl) | pyrrolidino |
| Cl | H | H | CF3 | H | NO2 | NO2 | S | —CH3 | SCH2CH2SCH2CH2 |
| Cl | H | H | CF3 | H | NO2 | NO2 | O | —OCH2CH2CH2O— | |
| Cl | H | H | CF3 | H | NO2 | NO2 | O | —O—CH(CH2)—CH(CH2)—O— with CH2—CH2 bridge | |
| Cl | H | H | CF3 | H | NO2 | NO2 | O | —O—C6H4—CH2O— (benzodioxole-type) | |
| Cl | H | H | CF3 | H | NO2 | NO2 | O | —O—C6H4—O— (catechol-type) | |

| R1 | R2 | R3 | R4 | R5 | R6 | R7 | X | Y1 | Y2 |
|---|---|---|---|---|---|---|---|---|---|
| Cl | H | H | CF3 | H | NO2 | NO2 | O | OC(CH3)=CHCOCH3 | OCH3 |
| Cl | H | H | CF3 | H | NO2 | NO2 | O | OCHBrCBrCl2 | OCH3 |
| Cl | H | H | CF3 | H | NO2 | NO2 | S | OCH2CH2SC2H5 | OCH3 |
| Cl | H | H | CF3 | H | NO2 | NO2 | S | OCH(CH3)CH2SCH(CH3)CH(CH3)CN | OCH3 |
| Cl | H | H | CF3 | H | NO2 | NO2 | S | SCHCO2C2H5 / CH2CO2H | OCH3 |
| Cl | H | H | CF3 | H | NO2 | NO2 | O | CF3 | CF3 |
| Cl | H | H | CH3 | H | NO2 | NO2 | O | CH2CCl3 | CH2CCl3 |
| Cl | H | H | CF3 | H | NO2 | NO2 | O | (CH2)4OCH3 | (CH2)4OCH3 |
| Cl | H | H | CF3 | H | NO2 | NO2 | O | CH2CH2CN | CH2CH2SCH3 |
| Cl | H | H | CF3 | H | NO2 | NO2 | O | CH2CH=CH3 | CH2CH=CH2 |
| Cl | H | H | CF3 | H | NO2 | NO2 | O | CH=CCl2 | CH=CCl2 |
| Cl | H | H | CF3 | H | NO2 | NO2 | O | CH=CHCO2CH3 | CH2C6H5 |
| Cl | H | H | CF3 | H | NO2 | NO2 | S | CH2—C6H4—CH3 | CH2—C6H4—CF3 |
| Cl | H | H | CF3 | H | NO2 | NO2 | S | SCF3 | SCF3 |
| Cl | H | H | CF3 | H | NO2 | NO2 | S | SCHBrCCl2H | SCHBrCCl2H |

TABLE I-continued

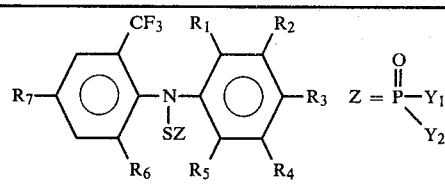

| R₁ | R₂ | R₃ | R₄ | R₅ | R₆ | R₇ | X | Y₁ | Y₂ | m.p. °C. |
|---|---|---|---|---|---|---|---|---|---|---|
| Cl | H | H | CF₃ | H | NO₂ | NO₂ | O | OCH₃ | OCH₃ | |
| Cl | H | H | CF₃ | H | NO₂ | NO₂ | S | SCH₃ | SCH₃ | |
| Cl | H | H | CF₃ | H | NO₂ | NO₂ | O | C₆H₅ | SCH₃ | |
| Cl | H | H | CF₃ | H | NO₂ | NO₂ | O | CH₃ | CH₃ | |
| Cl | H | H | CF₃ | H | NO₂ | NO₂ | O | n-Bu | n-Bu | |
| Cl | H | H | CF₃ | H | NO₂ | NO₂ | S | —O—C₆H₄—O— | | |

Formulation

Useful formulations of the compounds of Formula (I) can be prepared in conventional ways. They include dusts, solutions, suspensions, emulsions, wettable powders, emulsifiable concentrates and the like. Many of these may be applied directly to the plant. Sprayable formulations can be extended in suitable media and used at spray volumes of from a few pints to several hundred gallons per acre. High-strength compositions are primarily used as intermediates for further formulation. The formulations, broadly, contain about 1% to 99% by weight of active ingredient(s) and at least one of (a) about 0.1% to 20% surfactant(s) and (b) about 1% to 99% solid or liquid diluent(s). More specifically, they will contain these ingredients in the following approximate proportions:

|  | Percent by Weight | | |
|---|---|---|---|
|  | Active Ingredient | Diluent(s) | Surfactant(s) |
| Wettable Powders | 20–90 | 0–74 | 1–10 |
| Oil Suspensions, Emulsions, Solutions (including Emulsifiable Concentrates) | 5–50 | 40–95 | 0–15 |
| Aqueous Suspensions | 10–50 | 40–84 | 1–20 |
| Dusts | 1–25 | 70–99 | 0–5 |
| Granules and Pellets | 1–95 | 5–99 | 0–15 |
| High-Strength Compositions | 90–99 | 0–10 | 0–2 |

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins, et al., "Handbook of Insecticide Dust Diluents and Carriers", 2nd Edn., Dorland Books, Caldwell, N.J. The more absorptive diluents are preferred for wettable powders and the denser ones for dusts. Typical liquid diluents and solvents are described in Marsden, "Solvents Guide", 2nd Edn., Interscience, New York, 1950. Solubility under 0.1% is preferred for suspension concentrates; solution concentrates are preferably stable against phase separation at 0° C. "McCutcheon's Detergents and Emulsifiers Annual", MC Publishing Co., Ridgewood, New Jersey, as well as Sisely and Wood, "Encyclopedia of Surface Active Agents", Chemical Publ. Co., Inc., New York, 1964, list surfactants and recommended uses. All formulations can contain minor amounts of additives to reduce foam, caking, corrosion, microbiological growth, promote sticking, etc. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084).

For further information regarding the art of formulation, see for example:

J. B. Buchanan, U.S. Pat. No. 3,576,834, Apr. 27, 1971, Col, 5, Line 36 through Col. 7, Line 70 and Ex. 1–4, 17, 106, 123–140;

R. R. Shaffer, U.S. Pat. No. 3,560,616 Feb. 2, 1971, Col. 3, Line 48 through Col. 7, Line 26 and Examples 3–9, 11–18;

E. Somers, "Formulation", Chapter 6 in Torgeson, "Fungicides", Vol, I, Academic Press, New York, 1967.

Utility

The compounds of this invention may be used in several ways. First, they are active as miticides and mite ovicides and may be used to protect plants from damage caused by these pests. More specifically, fruits, field crops, vegetables and ornamentals can be protected.

When mite eggs or mites come into contact with the compounds of this invention, either in the form of direct spray or in the case of motile forms by walking over treated surfaces, they are killed if they have been exposed to a sufficiently high dosage. While most plants are able to tolerate the presence of very small numbers of mites without adverse effect, the reproductive capacity of these pests is enormous. Generally, mite populations rapidly build up, easily out-stripping parasite and predator capabilities for control. Growers noting rapid mite build-up must take immediate action to prevent damage to economically important crops.

The method of this invention, namely, contacting mites or mite eggs with an effective concentration, is a most desirable method for control of these pests. This may be accomplished by applying an effective amount of a compound of this invention to the locus of infestation, to the area to be protected or to the pests themselves.

The quantity of compound needed for miticidal activity will vary depending on the specific situation; generally, a very small quantity is required. Among the variables that must be considered in deciding on the quantity of chemical to be used are the specific compound itself, the specific mite to be controlled, weather conditions, the type of crop, the stage of development of the crop, the volume of spray applied, population pressure, and the interval between applications. For plant protection, solutions or suspensions contain as little as 2.5 ppm of active ingredient in a spray solution may prove effective in a given set of circumstances. For field usage, however, in high-volume applications, aqueous spray preparations containing 5–2500 ppm of active ingredient are generally useful. Preferred are suspensions containing 20–500 ppm, and most preferred are those containing 80–320 ppm. On an area basis, in general, 0.03 to 5.5 kilograms of active ingredient per hectare are acceptable, preferably 0.03 to 3 kilograms, and most preferably, 0.06 to 2 kg. When applied in an orchard, spraying is continued until run-off is observed.

The compounds are especially suited for the protection of living plants such as fruit-bearing trees, nut-bearing trees, ornamental trees, forest trees, vegetable crops, horticultural crops (including ornamentals, small fruits and berries) and grain and seed crops. Apple trees, peach tree, cotton, citrus trees, bean and peanuts are particularly susceptible to mite damage and can be protected by application of the compounds of this invention. To assure control throughout the growing season (e.g., June through August in the Northern Hemisphere) multiple applications at desired intervals can be utilized.

Many species of mites are controlled by the compounds of this invention. The following is a list of representative susceptible mites along with the types of damage that they can cause: *Panonychus ulmi* (European red mite) and *Tetranychus urticae* (two-spotted mite) which are commonly called "orchard mites", and which attack a great many deciduous trees, such as apple, pear, cherry, plum and peach trees; *Tetranychus atlanticus* (Atlantic or strawberry mite), *T. cinnabarinus* (carmine spider mite) and *T. pacificus* (Pacific mite); which attack cotton and numerous other crop plants; *Paratetranychus citri* (citrus red mite) and others which attack citrus; *Phyllocoptruta oleivora* which causes citrus rust; *Byrobia praetiosa* (clover mite) which attacks clover, alfalfa and other crops; and *Aceria Neocynodomis* which attacks grasses and other plants.

The compounds of this invention are useful for the control of insects throughout their various developmental stages. The insects or insect eggs are controlled by applying the material in a convenient formulation to the locus of infestation, to the area to be protected, or to the pests themselves. For the control of insects in agricultural crops, the compound is generally applied to the foliage or other plant parts which are to be protected. Effective amounts to be applied depend on the species to be controlled, its life stage, its size and location and other variables. In general, 0.1 to 10 kg/ha may be required for insect control in agriculture with rates of 0.25 to 4 kg/ha usually being sufficient. Preferably rates in large scale operations are in the range of 0.3 to 2 kg/ha.

The insect species that may be controlled during their various developmental stages by the insecticidal action of the compounds of this invention include, but are not limited to, *Spodoptera exigua* (beet armyworm), *Spodoptera eridania* (southern armyworm), *Spodoptera frugiperda* (fall armyworm), *Heliothis zea* (bollworm), *Heliothis virescens* (tobacco budworm), and Trichoplusia ni (cabbage looper).

These compounds are especially useful for controlling adult mosquitos, mosquito larvae, and ticks including, but not limited to, *Rhipicephalus sanguineus* (brown dog tick) and *Dermacentor variabiles* (American dog tick).

Motile stages of insects that may be controlled include, but are not limited to, *Aphis fabae* (bean aphid), *Myzus persicae* (green peach aphid), *Melanopus femurrubrum* (redlegged grasshopper), and *Musca domestica* (house fly).

The compounds of this invention are also useful as plant disease control agents. They are effective for the control of a broad spectrum of plant diseases as represented by, but not limited to, soil-borne fungal pathogen *Rhizoctonia solani*, foliar pathogens, *Puccinia graminis*, *Erisyphe cichoracearum*, *Venturia inaequalis* and *Phytophthora infestans*, and the seedborne fungus *Helminthosporium oryzae*. Diseases of a wide variety of ornamental, vegetable, cereal and fruit crops are controlled by the compound of this invention.

Disease control is accomplished by applying the compounds to the portion of the plant to be protected, such as the roots, stems, foliage, fruit, seeds, tubers or bulbs, or to the media (soil or sand) in which the plants to be protected are growing. The compounds may also be applied to the seed from which the plants to be protected are to be grown.

Rates of application for the compounds will be influenced by many factors of the environment and must be determined under use conditions. Foliage can normally be protected when treated at a rate of from 1 to 500 ppm of active ingredient. Plants growing in soil treated at a concentration of from 0.1 to about 20 kg/ha can be protected from disease. Seed and seedlings can normally be protected when seed is treated at a rate of from 0.06 to about 3 grams per kilogram of seed.

What is claimed is:

1. A compound of the formula

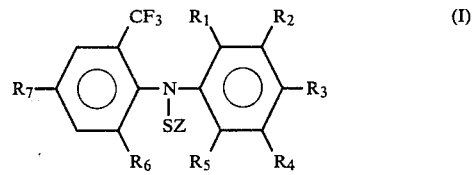

wherein $R_1$, $R_3$ and $R_4$ are independently H, F, Cl, Br, $NO_2$, $CF_3$, $OCHF_2$, $OCF_3$, $OCF_2CF_2H$ or $S(O)_kR_8$; or $R_3$ and $R_4$ may be taken together to form —$OCF_2O$— or —$OCF_2OCF_2$—;

$R_2$ is H, F, Cl, Br, $NO_2$, $CF_3$ or $S(O)_kR_8$;

$R_5$ is H, Cl, F, Br or $NO_2$;

$R_6$ is H, $NO_2$ or $CF_3$;

$R_7$ is $NO_2$ or $CF_3$; k is 0, 1 or 2;

$R_8$ is $C_1$–$C_2$ alkyl optionally substituted with 2–4 Cl and/or F;

Z =

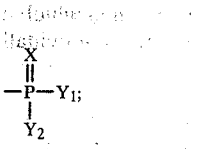

X is O or S;

$Y_1$ or $Y_2$ are independently: $C_1$–$C_4$ alkyl optionally substituted with one or more F, Cl, Br or I, $OCH_3$, $OCH_2CH_3$, CN, $CH_3S$, $CH_3CH_2S$; $C_2$–$C_4$ alkenyl optionally substituted with one or more of F or Cl; $C_1$–$C_4$ alkoxy, optionally substituted with one to three atoms of F, Cl, Br, $CH_3O$, $CH_3CH_2O$ or combinations thereof; $C_1$–$C_4$ thioalkyl optionally substituted with one to three atoms of F, Cl, Br, I, or combinations thereof;

provided that (1) at least two of $R_1$, $R_2$, $R_3$, $R_4$ and $R_5$ are hydrogen;

(2) no more than two of the substituents $R_1$, $R_2$, $R_3$ and $R_4$ are simultaneously $NO_2$ or $CF_3$;

(3) when two $NO_2$ or two $S(O)_kR_8$ groups are present, they are not ortho to one another;

(4) $R_6$ and $R_7$ are not simultaneously $CF_3$; and (5) further provided that when $R_6$ is $NO_2$, then (a) $R_1$ is H, F or Cl when $R_3$ is other than H, F or Cl;

(b) when $R_1 = R_3 = R_5$, then $R_1$, $R_3$ and $R_5$ are either H or F; and (c) $R_5$ is either H or F.

2. A compound of claim 1 wherein $R_1$ is F, Cl, Br, $CF_3$, $OCHF_2$, $OCF_3$, $OCF_2CF_2H$ or $S(O)_kCF_3$.

3. A compound of claim 1 wherein $R_2$ is H, F, Cl or Br.

4. A compound of claim 1 wherein $R_3$ is H, F, Cl, Br or $S(O)_kCF_3$.

5. A compound of claim 1 wherein $R_4$ is F, Cl, Br, $CF_3$, $OCHF_2$, $OCF_3$, $OCF_2CF_2H$ or $S(O)_kCF_3$.

6. A compound of claim 1 wherein $R_6$ is $NO_2$.

7. A compound of claim 1 wherein $R_1$ and $R_4$ are independently Cl, $CF_3$, $OCF_3$, $OCF_2CF_2H$ or $S(O)_kCF_3$.

8. A compound of claim 1 wherein $R_3$ is H or $S(O)_kCF_3$.

9. A compound of claim 1 wherein $R_2$ and $R_5$ are H.

10. A compound of claim 1 wherein $R_6$ and $R_7$ are $NO_2$.

11. A compound of claim 10 wherein $R_1$ and $R_4$ are independently Cl, $CF_3$, $OCF_3$, $OCF_2CF_2H$ or $S(O)_kCF_3$;

$R_3$ is H or $S(O)_kCF_3$;

$R_2$ and $R_5$ are H;

$R_6$ and $R_7$ are $NO_2$

12. A compound of claim 11 wherein $Y_1 = Y_2$.

13. A compound of claim 12 wherein $Y_1$ is $CH_3O$, $CH_3CH_2O$, $CH_3S$, $CH_3CH_2S$,

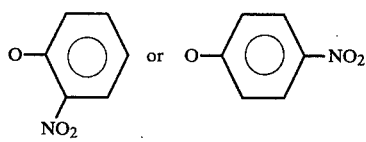

14. A compound of claim 13 wherein X is O.

15. An agricultural composition comprising an effective amount of surfactant, diluent or mixture thereof and a compound of claim 1.

16. An agricultural composition comprising an effective amount of surfactant, diluent or mixture thereof and a compound of claim 2.

17. An agricultural composition comprising an effective amount of surfactant, diluent or mixture thereof and a compound of claim 2.

18. An agricultural composition comprising an effective amount of surfactant, diluent or mixture thereof and a compound of claim 3.

19. An agricultural composition comprising an effective amount of surfactant, diluent or mixture thereof and a compound of claim 4.

20. An agricultural composition comprising an effective amount of surfactant, diluent or mixture thereof and a compound of claim 6.

21. An agricultural composition comprising an effective amount of surfactant, diluent or mixture thereof and a compound of claim 7.

22. An agricultural composition comprising an effective amount of surfactant, diluent or mixture thereof and a compound of claim 8.

23. An agricultural composition comprising an effective amount of surfactant, diluent or mixture thereof and a compound of claim 9.

24. An agricultural composition comprising an effective amount of surfactant, diluent or mixture thereof and a compound of claim 10.

25. An agricultural composition comprising an effective amount of surfactant, diluent or mixture thereof and a compound of claim 11.

26. An agricultural composition comprising an effective amount of surfactant, diluent or mixture thereof and a compound of claim 12.

27. An agricultural composition comprising an effective amount of surfactant, diluent or mixture thereof and a compound of claim 13.

28. An agricultural composition comprising an effective amount of surfactant, diluent or mixture thereof and a compound of claim 14.

29. A method for control of mites, insects, fungus, mite eggs or insect eggs which comprises applying to a locus to be protected a miticidally, insecticidally, fungicidally or ovicidally effective amount of a compound of claim 1.

30. A method for control of mites, insects, fungus, mite eggs or insect eggs which comprises applying to a locus to be protected a miticidally, insecticidally, fungicidally or ovicidally effective amount of a compound of claim 2.

31. A method for control of mites, insects, fungus, mite eggs or insect eggs which comprises applying to a locus to be protected a miticidally, insecticidally, fungicidally or ovicidally effective amount of a compound of claim 3.

32. A method for control of mites, insects, fungus, mite eggs or insect eggs which comprises applying to a locus to be protected a miticidally, insecticidally, fungicidally or ovicidally effective amount of a compound of claim 4.

33. A method for control of mites, insects, fungus, mite eggs or insect eggs which comprises applying to a locus to be protected a miticidally, insecticidally, fungicidally or ovicidally effective amount of a compound of claim 5.

34. A method for control of mites insects, fungus, mite eggs or insect eggs which comprises applying to a locus to be protected a miticidally, insecticidally, fungicidally or ovicidally effective amount of a compound of claim 6.

35. A method for control of mites, insects, fungus, mite eggs or insect eggs which comprises applying to a locus to be protected a miticidally, insecticidally, fungicidally or ovicidally effective amount of a compound of claim 7.

36. A method for control of mites, insects, fungus, mite eggs or insect eggs which comprises applying to a locus to be protected a miticidally, insecticidally, fungicidally or ovicidally effective amount of a compound of claim 8.

37. A method for control of mites, insects, fungus, mite eggs or insect eggs which comprises applying to a locus to be protected a miticidally, insecticidally, fungicidally or ovicidally effective amount of a compound of claim 9.

38. A method for control of mites, insects, fungus, mite eggs or insect eggs which comprises applying to a locus to be protected a miticidally, insecticidally, fungicidally or ovicidally effective amount of a compound of claim 10.

39. A method for control of mites, insects, fungus, mite eggs or insect eggs which comprises applying to a locus to be protected a miticidally, insecticidally, fungicidally or ovicidally effective amount of a compound of claim 11.

40. A method for control of mites, insects, fungus, mite eggs or insect eggs which comprises applying to a locus to be protected a miticidally, insecticidally, fungicidally or ovicidally effective amount of a compound of claim 12.

41. A method for control of mites, insects, fungus, mite eggs or insect eggs which comprises applying to a locus to be protected a miticidally, insecticidally, fungicidally or ovicidally effective amount of a compound of claim 13.

42. A method for control of mites, insects, fungus, mite eggs or insect eggs which comprises applying to a locus to be protected a miticidally, insecticidally, fungicidally or ovicidally effective amount of a compound of claim 14.

43. The compound of claim 1 wherein
$R_1=Cl$; $R_2=H$; $R_3=H$; $R_4=CF_3$, $R_5=H$; $R_6=NO_2$, $R_7=NO_2$;
$Y_1=OCH_2CH_3$; $Y_2=OCH_2CH_3$; and $X=O$.

44. An agricultural composition comprising an effective amount of surfactant, diluent or mixtures thereof and the compound of claim 43.

45. A method for control of mites, insects, fungus, mite eggs or insect eggs which comprises applying to a locus to be protected a miticidally, insecticidally, fungicidally or ovicidally effective amount of the compound of claim 43.

* * * * *